United States Patent
Bencteux et al.

(10) Patent No.: US 9,636,479 B2
(45) Date of Patent: May 2, 2017

(54) MEDICAL ROBOT IN PARTICULAR FOR GUIDING ELONGATE FLEXIBLE MEDICAL PARTS

(71) Applicant: ROBOCATH, Rouen (FR)

(72) Inventors: Philippe Bencteux, St Martin du Vivier (FR); Sébastien Deboeuf, Herblay (FR); Jacques Marignier, Le Mesnil Esnard (FR)

(73) Assignee: ROBOCATH, Rouen (FR)

( * ) Notice: Subject to any disclaimer, the term of this patent is extended or adjusted under 35 U.S.C. 154(b) by 0 days.

(21) Appl. No.: 14/772,600

(22) PCT Filed: Mar. 7, 2014

(86) PCT No.: PCT/FR2014/050528
§ 371 (c)(1),
(2) Date: Sep. 3, 2015

(87) PCT Pub. No.: WO2014/135814
PCT Pub. Date: Sep. 12, 2014

(65) Prior Publication Data
US 2016/0008574 A1    Jan. 14, 2016

(30) Foreign Application Priority Data
Mar. 7, 2013 (FR) ...................... 13 52063

(51) Int. Cl.
*A61M 25/01* (2006.01)
*A61M 25/00* (2006.01)
(Continued)

(52) U.S. Cl.
CPC ......... *A61M 25/0113* (2013.01); *A61B 34/30* (2016.02); *A61B 2034/301* (2016.02); *A61B 2090/376* (2016.02); *A61M 25/002* (2013.01)

(58) Field of Classification Search
CPC .................................................. A61M 25/0113
(Continued)

(56) References Cited

U.S. PATENT DOCUMENTS 3,995,628 A    12/1976   Gula
7,389,156 B2 *  6/2008   Ziegler .............. A22C 17/0013
                                                    318/568.1
(Continued)

FOREIGN PATENT DOCUMENTS

EP    1 576 930 A1    9/2005
EP    1 792 638 A2    6/2007
FR    2 308 381 A1   11/1976

OTHER PUBLICATIONS

French Search Report Application No. 1352063, reported on Nov. 15, 2013.
(Continued)

*Primary Examiner* — David S Luo
(74) *Attorney, Agent, or Firm* — Miller, Matthias & Hull LLP

(57) ABSTRACT

The invention concerns a medical robot for guiding elongate flexible medical parts, comprising: a fixed base having an outer peripheral wall; a container which is movable relative to the fixed base by a degree of freedom of rotation, the container comprising an inner peripheral wall defining with the outer peripheral wall a first compartment; and the outer peripheral wall having an aperture which opens into the interior of the first compartment and via which the first elongate flexible part can be moved.

15 Claims, 5 Drawing Sheets

(51) Int. Cl.
 *A61B 34/30* (2016.01)
 *A61B 90/00* (2016.01)
(58) Field of Classification Search
 USPC ............ 318/560, 567, 568.1, 568.11, 568.12
 See application file for complete search history.

(56) References Cited

U.S. PATENT DOCUMENTS

| | | |
|---|---|---|
| 7,620,476 B2 * | 11/2009 | Morse ........................ A47L 5/14 15/319 |
| 7,927,310 B2 | 4/2011 | Bencteux |
| 2005/0004579 A1 | 1/2005 | Schneider |
| 2009/0082722 A1 | 3/2009 | Munger |
| 2013/0172738 A1 | 7/2013 | Bencteux |

OTHER PUBLICATIONS

International Search Report Application No. PCT/US2014/050528, reported on Jun. 23, 2014.

* cited by examiner

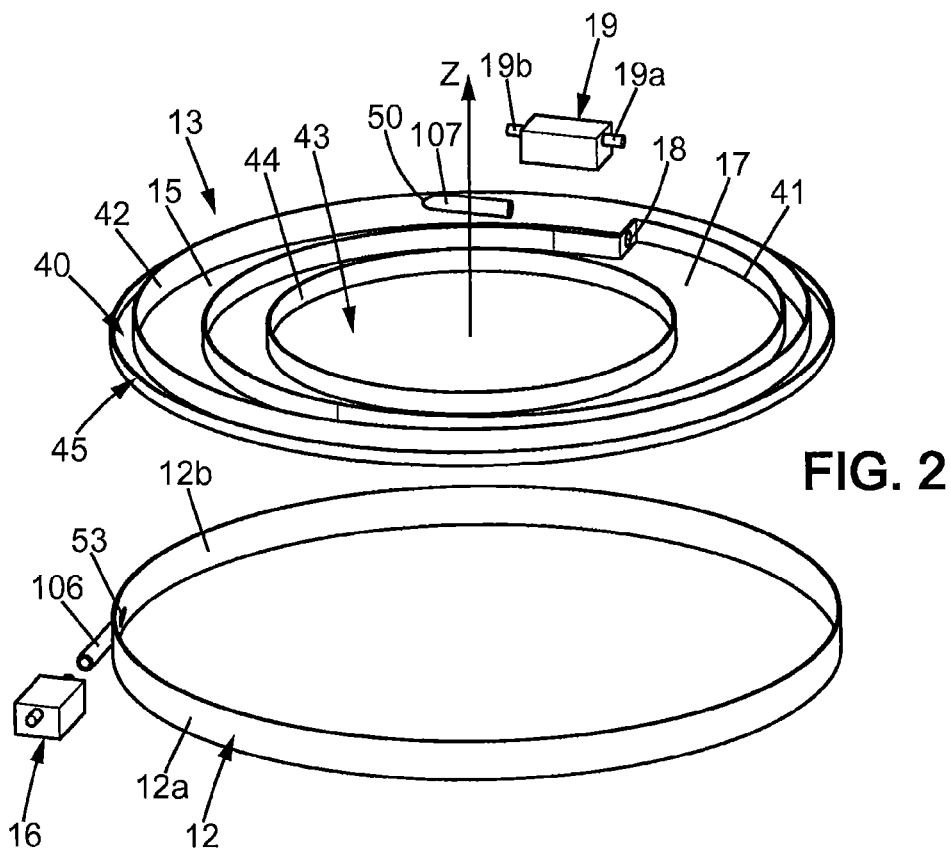
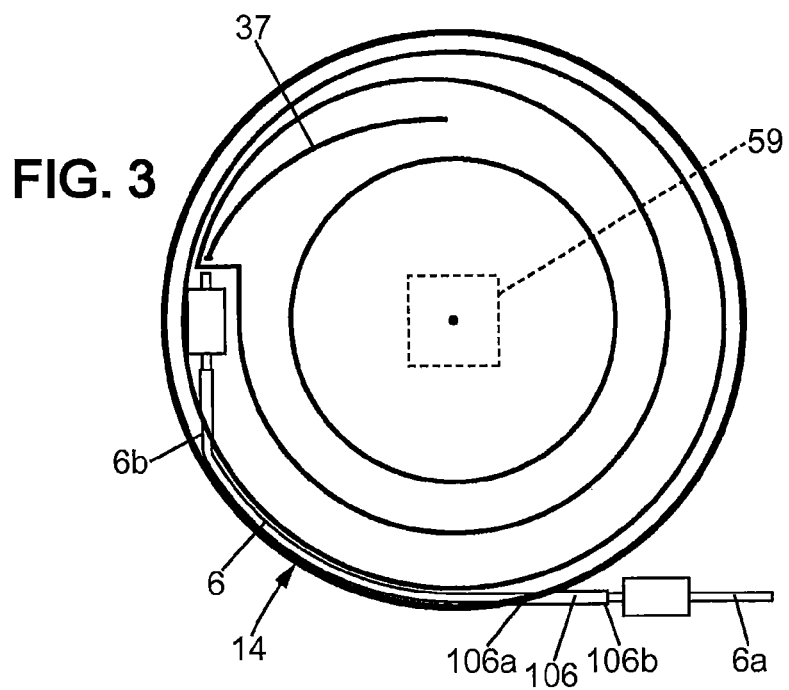

MEDICAL ROBOT IN PARTICULAR FOR GUIDING ELONGATE FLEXIBLE MEDICAL PARTS

CROSS-REFERENCE TO RELATED APPLICATION

This Application is a 35 USC §371 US National Stage filing of International Application No. PCT/FR2014/050528 filed on Mar. 7, 2014, and claims priority under the Paris Convention to French Patent Application No. 13 52063 filed on Mar. 7, 2013.

FIELD OF THE DISCLOSURE

The present invention relates to medical robots, particularly robots used to control the introduction of catheters into the body of a patient.

BACKGROUND OF THE DISCLOSURE

A catheter is a typical example of an elongate flexible medical part to be introduced into the body of a patient. Such a catheter is inserted into a tubular anatomical opening of a patient, and therefore must be relatively flexible. The catheter tip must also get to a patient's internal organ, so therefore must be relatively elongated. Other examples of elongate flexible medical parts are, for example, a guide, which is of smaller diameter and generally placed inside the catheter on which said catheter slides, or an interventional catheter, also arranged inside the catheter, having a tip providing some medical function such as a surgical tool (clamp, balloon, etc.).

The insertion of such catheters is usually monitored using X-rays. This results in radiation exposure for a physician who repeatedly performs such insertions.

Efforts have been made to automate this insertion. The catheter is then manipulated by a robot which is controlled remotely by the physician, still under X-ray guidance but from a room not exposed to, radiation.

Document U.S. Pat. No. 7,927,310 describes an example of such a system.

This system has the great advantage of being well suited for maintaining the sterility of catheters or other members introduced into the patient, which are bathed in preservative liquid such as normal saline solution. This robot is quite satisfactory. However, we are always looking to simplify the design of such a robot without reducing its performance, especially in terms of reliability.

SUMMARY OF THE DISCLOSURE

To this end, the invention relates to a medical robot for guiding elongate flexible medical parts, comprising:
a fixed base having an outer peripheral wall,
a container which is movable relative to the fixed base by a degree of freedom of rotation, the container comprising an inner peripheral wall defining with the outer peripheral wall a first compartment, the container comprising a second compartment integral with the inner peripheral wall,
the first and second compartments being adapted for respectively receiving first and second elongate flexible parts to be inserted into a tubular passage of a patient,
the first compartment comprising an entry capable of being assembled to an end of the first elongate flexible part,
the second compartment comprising an exit associated with the entry of the first compartment, the second elongate flexible part being movable through the exit and the entry so as to extend into the first hollow tubular elongate flexible part,
the outer peripheral wall having an aperture which opens into the interior of the first compartment, through which the first elongate flexible part can be moved.

With these arrangements, a degree of freedom has been eliminated without interfering with operation of the robot. This simplification reduces the number of motors and controls, and therefore the risk of breakdown which must systematically be avoided in this context.

In preferred embodiments of the invention, one or more of the following arrangements may possibly be used:
the degree of freedom is a rotation about a vertical axis;
the medical robot comprises a drive module adapted to generate movement of the second elongate flexible part relative to the container (13) by at least a degree of freedom;
the exit is associated with the entry via the drive module;
a hollow introducer tube comprises a first end integral in translation with the inner peripheral wall, and which can be assembled to said first end of the first elongate flexible part, and a second end assembled to an exit of the drive module;
the second compartment comprises an outer peripheral wall, and an intermediate space is defined between the outer peripheral wall of the second compartment and the inner peripheral wall, the drive module being housed within the intermediate space;
the drive module is a second drive module, the medical robot further comprising a first drive module adapted to generate movement of the first elongate flexible part relative to the fixed base by at least a degree of freedom;
the first drive module is assembled to the aperture;
the medical robot comprises a motor adapted to drive the container along the degree of freedom, the second drive module and the motor being enslaved one to one another;
the hollow introducer tube is a second hollow introducer tube, and a first hollow introducer tube comprises a first end secured to the outer peripheral wall and assembled to the aperture, and a second end assembled to the first drive module;
each drive module can be operated to generate one and/or the other among a translational movement of the respective elongate flexible part along its axis and a rotational movement of the respective elongate flexible part about its axis;
each drive module comprises a base defining an axis, and a mobile unit that is rotatable relative to the base with respect to this axis, the mobile unit comprising a movement application system that can be operated to generate translational movement of the respective elongate flexible part along this axis;
the fixed base and the container are in the form of consumable and/or sterilizable elements;
in a second configuration, the second compartment comprises an exit separated from the entry of the first compartment, the second elongate flexible part being movable through the exit to extend within the first hollow tubular elongate flexible part;
in the second configuration, a ramp guides the second elongate flexible part parallel to the first elongate flexible part and externally thereto.

Other features and advantages of the invention will be apparent from the following description of one of its embodiments, given by way of non-limiting example with reference to the accompanying drawings.

BRIEF DESCRIPTION OF THE DRAWINGS

In the drawings:

FIG. 2 is a perspective view of a robot in the system of FIG. 1,

FIG. 3 is a top view of FIG. 2,

In the various figures, the same references designate identical or similar elements.

DETAILED DESCRIPTION OF THE DISCLOSURE

Figure 1:
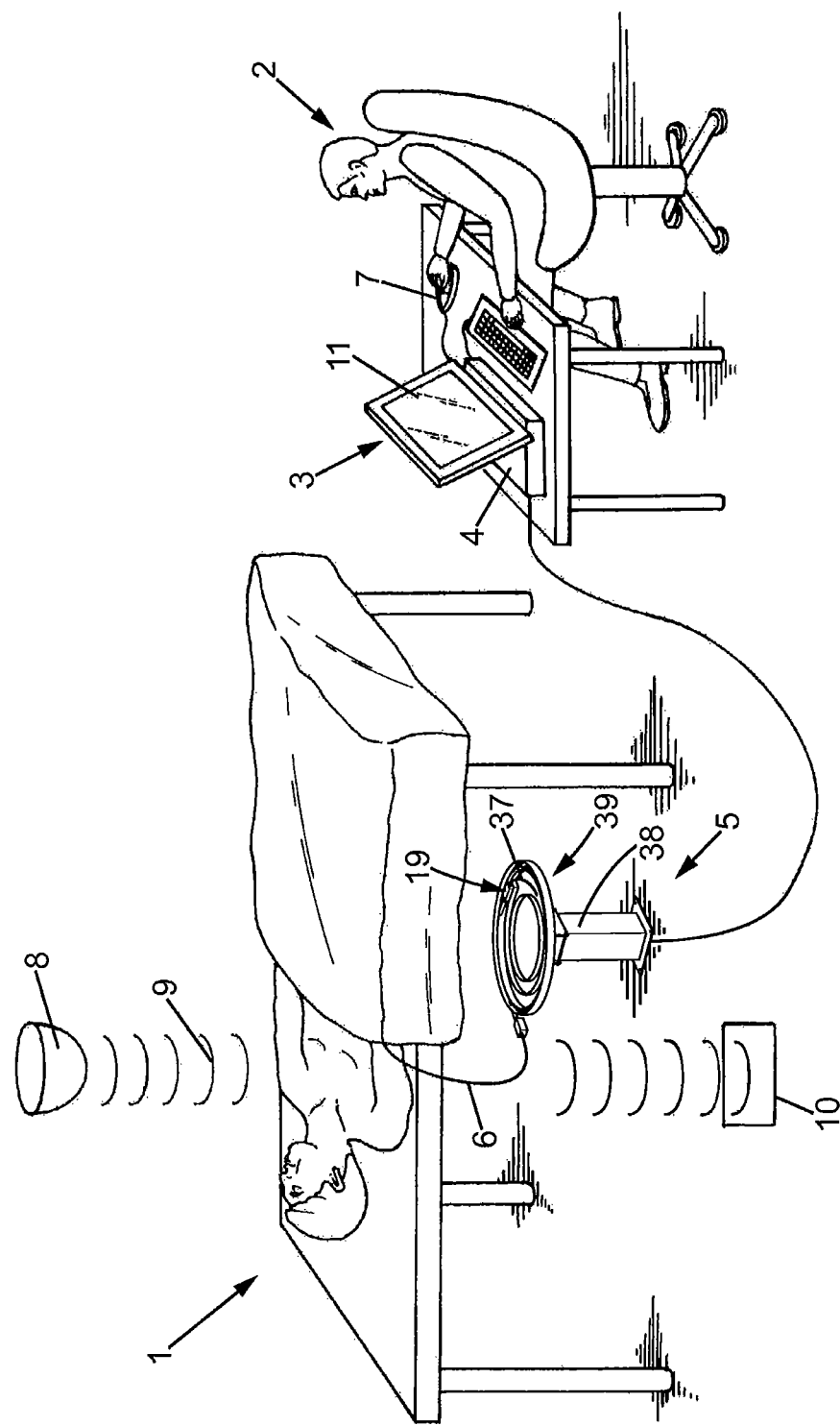
FIG. 1 is a schematic view of a robot-based automated system.

In FIG. 1, a patient 1 is undergoing an arteriography. This arteriography is being carried out by a person 2, for example a surgeon or qualified medical personnel, using an automated arteriography system 3 comprising for example a programmable machine 4 that remotely controls a robot 5 placed near the patient 1. The robot 5 is also sometimes referred to as a "winder/unwinder".

Movement of a catheter 6 within the patient's body 1 is controlled remotely by the qualified personnel 2 using a control means 7, such as a mouse or joystick for example, connected to the programmable machine 4.

The system further comprises an X-ray source 8 emitting X-rays 9 towards the patient 1, as well as an X-ray detector 10 able to detect the radiation passing through the patient 1. The detector 10 may be connected to the computer 4 to allow displaying the detected image on its screen 11.

The robot 5 has a vertical stand 38 and a horizontal plate 39 supported by this stand 38. The plate 39 is integral with a peripheral ring 12 having an outer peripheral wall 12a facing outward and an opposite outer peripheral wall 12b facing inward. "Outer" refers to the fact that the peripheral ring is radially distanced from the center of the plate 39.

The plate 39 carries a container 13 that is rotatable relative to the peripheral ring 12 about a vertical axis of rotation Z. An electric motor 59 can be used to control the rotation of the container 13 relative to the peripheral ring 12 about the axis Z.

In an advantageous arrangement, the peripheral ring 12 is provided with a skirt, in particular flexible, fixed for example by bonding or any other means on the outer peripheral wall 12a and at least partially covering the stand 38. Such a skirt forms in particular a sterility barrier between the elements of the robot which are intended to come in contact with the patient via an elongate flexible medical part, in particular the ring 12 and container 13, and which are in the form of consumable and/or sterilizable items, and the rest of the robot elements, particularly the stand 38, the motor 59, and other members of the system placed under the ring 12 in the vertical direction, which when sheltered by the sterile barrier will then not require repeated and costly sterilization operations. This sterile skirt is pierced only to allow fluidtight passage of various attachment means such as screws or other fasteners through these holes, to secure the elements placed above the skirt in the vertical direction, and of the shafts of the motors driving the movable elements of the robot, such as the container 13, placed above the skirt in the vertical direction. With these arrangements, the robot allows repeated use in a manner that is simple and inexpensive.

The container 13 comprises a bottom 43, for example horizontal, from which several dividing walls extend. The peripheral walls define a plurality of closed compartments integral to one another. The walls are peripheral and closed about axis Z. They extend vertically for example. The container 13 comprises, from the inside outwards, an inner compartment 17, an intermediate compartment 15, and an outer region 40, together forming a single piece. An inner peripheral wall 41 separates the inner compartment 17 from the intermediate compartment 15. An intermediate peripheral wall 42 separates the intermediate compartment 15 from the outer region 40. The outer region 40 comprises a peripheral rim 45 whose outwardly facing side 45a is of a shape complementary to the inwardly facing side 12b of the ring 12. In particular, these are two right circular cylindrical surfaces centered on axis Z.

The inner compartment 17 is defined by the inner peripheral wall 41 and the bottom 43 (or by a central cylindrical wall 44). The intermediate compartment 15 is defined by the inner peripheral wall 41, the bottom 43, and the intermediate peripheral wall 42.

An outer compartment 14 is defined by the bottom 43, the intermediate peripheral wall 42, the peripheral rim 45, and the ring 12.

Alternatively, it is not necessary to use an intermediate compartment 15, in which case the inner peripheral 41 and intermediate 42 walls can be combined.

The outer compartment 14 receives a tubular catheter 6 intended for insertion into an artery of a patient 1. The outer compartment 14 comprises an exit aperture 53 through which the catheter 6 can enter or exit the outer compartment 14. The exit aperture 53 is formed in the peripheral ring 12, and traverses it radially. It is arranged above the rim 45. A rigid guide tube 106 extends between the exit aperture and a drive mechanism 16. The catheter 6 is received inside the rigid guide tube 106. The catheter 6 extends from a first end 6a to a second end 6b along a lengthwise catheter direction. The outer compartment 14 is filled (to below the level of the rim 45 to avoid ring 12 leakage problems) with a preserving liquid bathing the catheter 6.

The drive mechanism 16 is carried by an arm fixedly connected to the stand 38, and is intended to be placed adjacent to the patient orifice to be catheterized. The position of the arm, in particular its height relative to the ground, can be adjusted if such is necessary for the requirements of the procedure.

Alternatively, the drive mechanism 16 may be carried by an arm fixedly connected to the ring 12, for example formed as one piece with the ring 12, or by an arm integral with the sterility skirt attached to the ring 12.

The drive mechanism is controlled by the surgeon 2 by means of the computer 4.

The rigid insertion tube 106 extends from a first end 106a connected to the aperture 53 at a second end connected to the drive mechanism 16.

The outer compartment 14 also comprises an entry aperture 50 providing access to the interior of the outer compartment 14 from an inner region. The entry aperture 50 is for example formed in the intermediate peripheral wall 42 and traverses it radially.

The second compartment 17 has an exit 18 through which a guide 37 contained in the second compartment has access to outside the second compartment, and in particular to the interior of the first compartment 14. In particular, it accesses the interior of the catheter contained in the first compartment. The exit aperture 18 is formed in the inner peripheral wall 41, and traverses it axially. A drive mechanism 19 extends into the intermediate compartment 42. It has an entry 19a for the guide 37 and an opposing exit 19b.

A rigid guiding introducer tube 107 extends between the exit 19b of the drive mechanism 19 and the entry aperture 50. It is sized to receive the guide 37 within its interior.

The second compartment 17 receives an elongate guide extending between a first and a second end along a lengthwise guide direction, and bathed in a suitable preserving liquid.

Figure 5A:
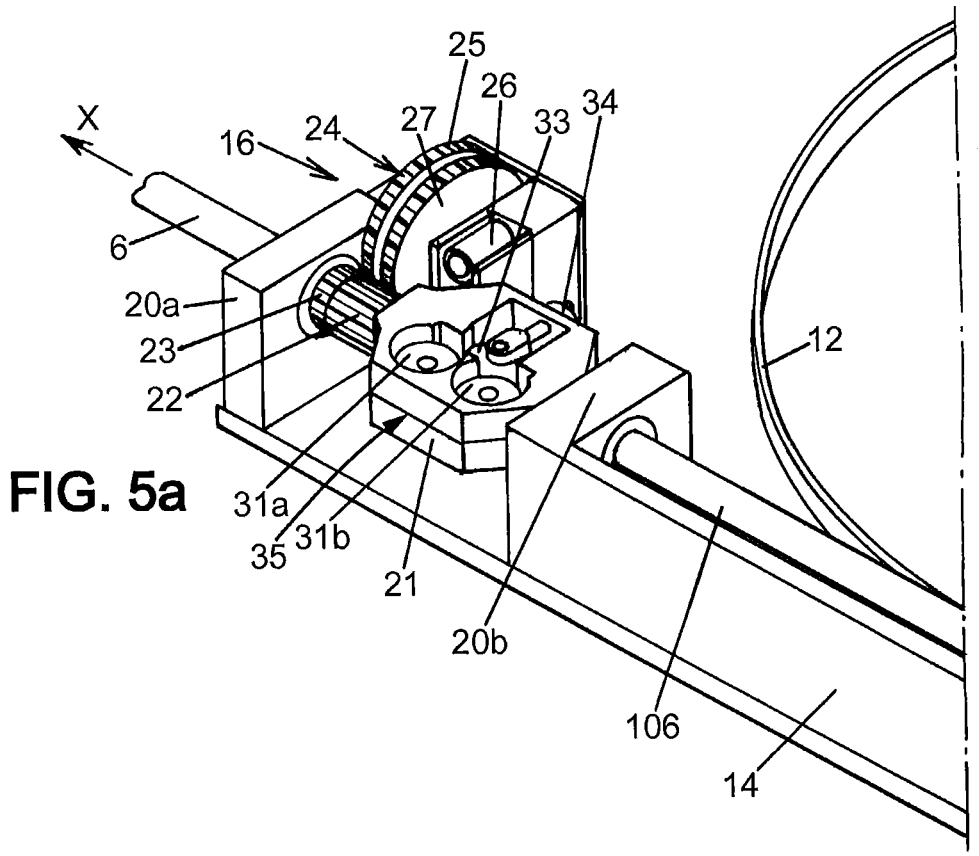
FIGS. 5a and 5b are perspective views of a drive module, respectively from above and from below.

FIG. 5a represents the first drive mechanism 16 according to an illustrative embodiment. The second drive mechanism 19 may be similarly implemented. The first drive mechanism 16 comprises a mobile unit 35 mounted so as to rotate relative to a base 20 about the lengthwise axis X of the catheter 6, within two bearings 20a, 20b of the base 20. The mobile unit comprises, in the example shown, a plate 21 carrying the catheter, and a cylindrical ring gear 23 rotatably mounted on a cylindrical axis 49 through which the catheter 6 passes on the inside.

The first drive mechanism 16 comprises an electric rotation motor 24 that drives the rotation, when electric current is applied, as controlled by the computer 4, of a rotation gear 25 which engages with the rotation ring gear 23 of the mobile unit.

The drive mechanism 16 also comprises an electric translation motor 26 that drives the rotation, when electric current is applied, as controlled by the computer 4, of a translation gear 27 which engages with the translation ring gear 22 mounted so as to rotate freely on the cylindrical shaft 49 integral with the rotation ring gear 23 through which the catheter 6 passes on the inside.

In a variant, it may be arranged that only a single motor is used, alternately coupled to one or the other of the rotation 25 and translation 27 gears. These motors are, for example, step motors, or DC or brushless motors.

These rotation 24 and translation 26 motors may advantageously be placed within the shelter of a sterility barrier, to allow reuse without requiring a sterilization operation.

In particular, in the case where the drive mechanism 16 is carried by an arm fixedly connected to the ring 12, or by an arm integral with the sterility skirt attached to the ring 12, the sterility skirt attached to the ring 12 may comprise holes to allow the fluidtight passage of attachment means, such as screws, for securing the base 20 to the arm, and holes to allow the fluidtight passage of the shafts of the rotation 24 and translation 26 motors.

Alternatively, the drive shafts of the rotation 24 and translation 26 motors may be designed as two parts rotationally coupled via a sealed rotatable coupling forming a sterility barrier between the two shaft portions and provided at the attachment arm of the drive module. In this variant, a first shaft portion located at the motor output is secured, preferably detachably, to an input ring rotatably mounted on a fixed plate, an element providing a dynamic seal being provided between the fixed plate and the input ring. This input ring has, on a side facing away from the first shaft portion, appropriate contours for engaging with complementary contours provided on the facing side of an output ring secured to the second shaft portion supporting a movement transfer element, such as a drive gear, for rotatably coupling the input ring and the output ring.

Figure 5B:
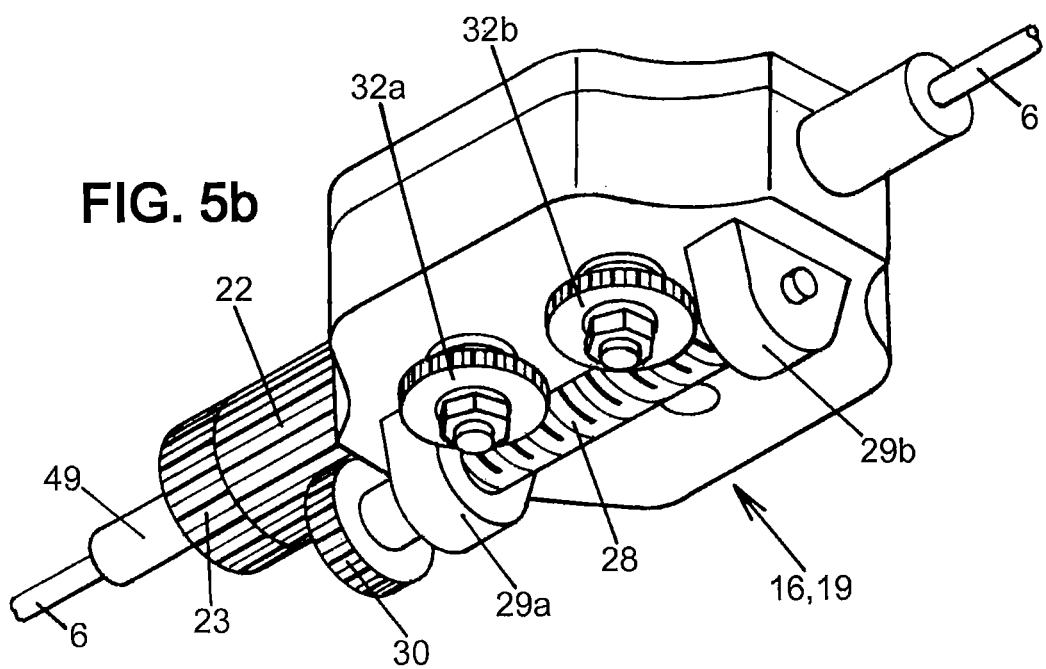

As represented in FIG. 5b, the translation gear ring 22 rotates a shaft 28, rotatably mounted in two bearings 29a and 29b, via an intermediate gear 30. The rotation of the shaft 28 about an axis parallel to axis X, causes rotation about axis Z of two drive wheels 31a and 31b arranged on the upper face of the plate (FIG. 5a), via corresponding gears 32a and 32b.

The catheter 6 is held in contact with the edge of the drive wheels 31 by a biasing roller 33, non-motorized, whose position relative to the plate is set via an adjustment mechanism 34 which allows adapting the drive mechanism 16 described herein to different catheter diameters. As the catheter is kept in engagement with the drive wheels 31a and 31b by the biasing roller 33, the rotation of these drive wheels causes displacement of the catheter along its lengthwise axis X.

Figure 4:
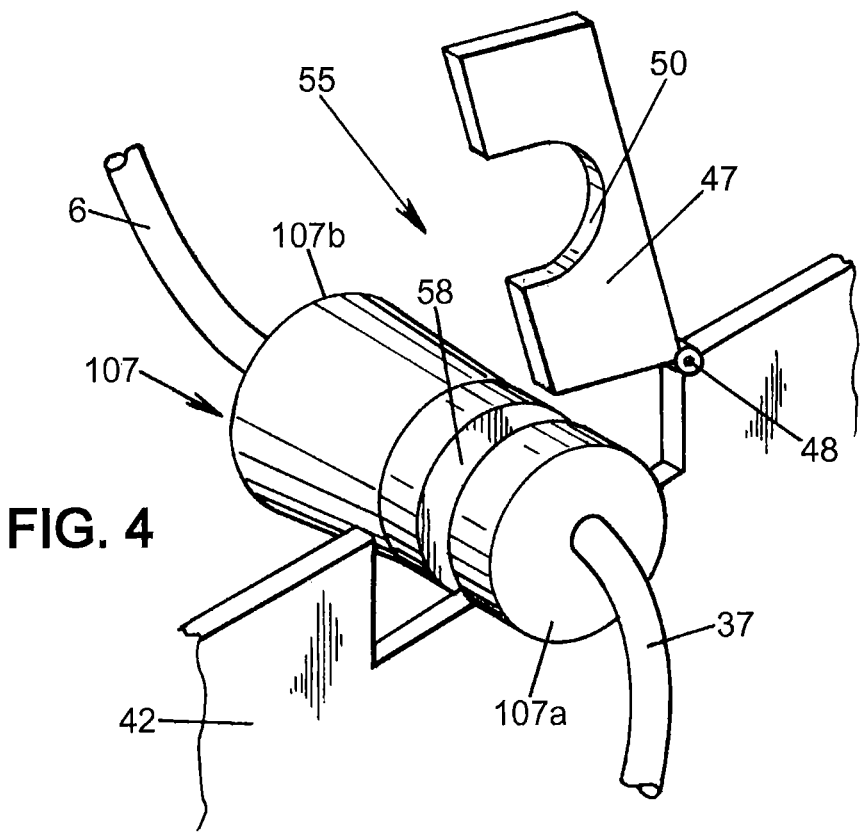
FIG. 4 is a perspective view of the details of one embodiment.

As represented in FIG. 2 and in more detail in FIG. 4, the exit 18 of the second compartment 17 is assembled to an attachment means 55. According to one purely illustrative example of the attachment means 55 represented in FIG. 4, the distal end of the catheter 6 is attached to the guide tube 107 which has a groove 58 fitting into the complementary entry aperture 50 formed in the intermediate peripheral wall 42. Half of this aperture 50 is formed in the intermediate peripheral wall 42, and half in a flap 47 that pivots for example on a hinge 48 on the intermediate peripheral wall 42. FIG. 4 shows the flap 47 in the open position, ready for insertion of the guide tube 107 into the aperture 59. The guide tube 107 is thus free to rotate relative to the intermediate peripheral wall 42 about a lengthwise axis of the guide 37. The introducer tube 107 is thus attached at a first end 107a to an exit 19b of the drive module 19, and at a second end 107b to the catheter 6.

This assembly allows the free rotation of the catheter 6 about its lengthwise axis relative the first compartment 14, and the integral movement of the catheter 6 and the second compartment 17 during translation of the catheter 6 along its lengthwise direction.

Alternatively, the flap could be replaced by an open ring secured to the wall.

An example use of the device represented in the above figures is now described. A surgeon punctures an artery, for example the femoral artery at the groin, and places a Desilet providing access to the artery. The robot 5 is positioned near the patient, and is connected to the computer 4. The robot 5 already contains a preserving liquid, bathing a catheter in the outer compartment 14 and a guide insertable into the catheter in the second compartment 17. By disengaging the roller 33 of the first drive mechanism 16, the catheter 6 can be moved by manual insertion by the surgeon, through the Desilet into the artery. Then, from the computer 4, the surgeon controls the electric translation motor of the second drive mechanism 19 to guide the guide 37 through the exit 18, inside the catheter 6, until the first end of the guide reaches the first end of the catheter, inside the patient.

During this operation, the X-ray source 8 can emit radiation which has no effect on the surgeon 2, and the image from the detector 10 can be displayed on the computer screen 11.

To enable the tip of the catheter to reach the area of interest inside the body of the patient 1, the surgeon 2 orders the following operations from the computer 4:

translation of the guide: by activating the electric translation motor 26 of the second drive mechanism 19, which causes rotation of the translation ring gear 22, the intermediate gear 30, the shaft 28, gears 32a and 32b and therefore drive wheels 31a and 31b which cause movement of the guide in translation along its lengthwise direction within the catheter 6, rotation of the guide about the longitudinal axis of the guide 1, by controlling the electric rotation motor 24 of the second drive mechanism 19, and thus the rotation gear 25 and the rotation gear ring 23 which causes rotation of the assembly of the mobile unit and the guide relative to the bearings 20a and 20b of the second system, and thereby that of the guide held on the mobile unit by the drive wheels 31a, 31b and the roller 33, translation of the catheter along the lengthwise catheter direction, controlled similarly to controlling the translation of the guide as described above, motor 59 and the electric translation motor 26 being enslaved to one another in a predetermined ratio, so that motor 59 rotates the container about axis Z as the catheter 6 moves in translation along its lengthwise direction, and rotation of the catheter, controlled as described above for the guide, the attachment means 55 allowing the catheter 6 to rotate about its lengthwise axis without affecting the guide 37 or container 13.

It may also be arranged that in certain embodiments, one can perform joint translation of the guide and of the catheter by controlling the motors simultaneously.

Control of both translation and rotation can of course be done in one direction or the other, to move the guide and the catheter to the site or to retract them.

A cover (not shown) may also be provided, assembled to the top of the ring 12 and covering the container 13, in particular to protect the ring prior to its placement in the operating room.

The system which has just been described, comprising the container 13, the ring 12, the drive modules 16 and 19, the guide 37, and the catheter 6, and the cover if there is one, is for example supplied as a sterile assembly ready for use, with the catheter already engaged in drive module 16 and the guide already engaged in drive module 19, for fast and simple attachment to the stand 38.

The various elements provided are disposable or reusable after sterilization.

Note that the tube 106 and the wall 12 may be slitted at the aperture 53, to enable emergency removal of the catheter 6 from the container 13 if needed.

Figure 6:
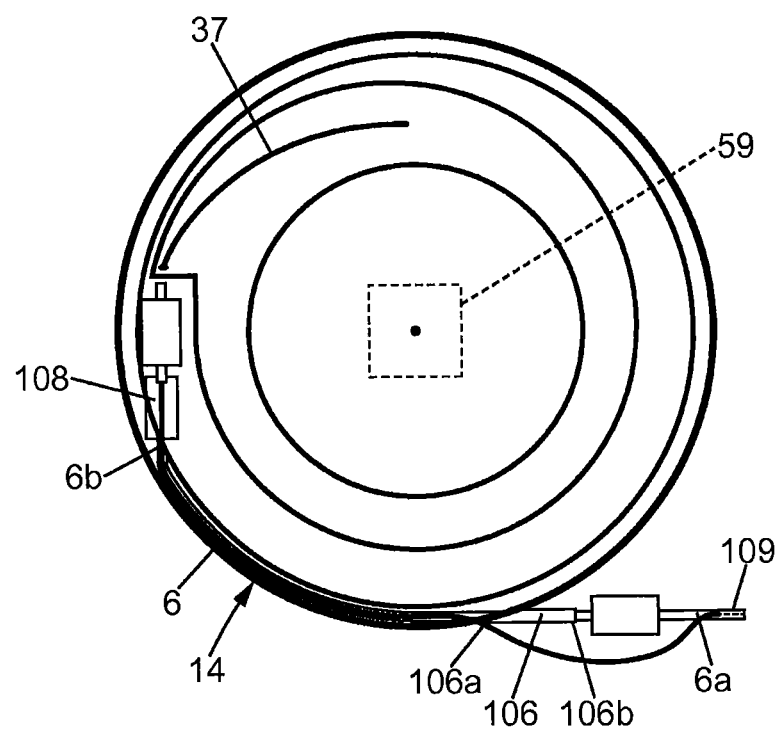
FIG. 6 is a figure similar to FIG. 3 for a configuration of the robot with an alternative configuration of the catheters.

According to a second embodiment, represented in FIG. 6, the same architecture of medical robot is used for an alternative catheter design. In this alternative catheter configuration, a "quick replacement" catheter is used. Such a catheter 6 has the feature that near its first end 6a, its wall has an insertion aperture 109 allowing the guide 37 to pass through the catheter 6 wall. Thus, according to one configuration, the guide 37 extends' coaxially with the catheter and inside the catheter, only in the region of the first end 6a, and may run outside the catheter 6 as well.

The insertion aperture is located, in the pre-surgery configuration, downstream of the drive module 16 for the catheter but upstream of the patient. During the procedure, it can be inside the patient. After the procedure, once the guide is removed, it can pass through the drive module 16 of the catheter.

In this configuration, it is therefore no longer necessary for the exit 18 of the second compartment 17 to be associated with the entry 50 of the first compartment. The exit 18 of the second compartment 17 can be separated from the entry 50 of the first compartment. It is sufficient to replace the guide tube 107 of the first embodiment with a guide ramp 108 which directs the guide 37 from the exit 19b of the drive mechanism 19 towards the insertion aperture 109 of the catheter. In the particular example represented, the guide ramp 108 leads the guide 37 from the exit 19b of the drive mechanism 19 to the first compartment 14 where the guide 37 runs parallel and externally to the catheter 6. Thus, the guide 37 exits the compartment 14 through the aperture 53 parallel to the catheter 6. An aperture may be provided in the end 106a of the tube 106 to avoid the passage of the guide inside the tube 106 as represented in FIG. 6.

The guide 37 is preferably guided to bypass the drive module 16 of the catheter. Thus, as represented, the guide travels outside the drive module 16 of the catheter between exit 19b (in particular between exit 53) and the insertion aperture 109.

In this embodiment, the entry 50 of the first compartment is then no longer an entry for the guide. However, the entry 50 of the first compartment retains its function of connecting the catheter 6 to the container.

Thus, simply by replacing the tube 107 with an appropriate ramp 108 (both are simple and disposable parts), one can use the same robot architecture for two alternative catheter designs.

The invention claimed is:

1. A medical robot for guiding elongate flexible medical parts, comprising:
 a fixed base having an outer peripheral wall,
 a container which is movable relative to the fixed base by a degree of freedom of rotation, the container comprising an inner peripheral wall defining with the outer peripheral wall a first compartment, the container comprising a second compartment integral with the inner peripheral wall,
 the first and second compartments being adapted for respectively receiving first and second elongate flexible parts to be inserted into a tubular passage of a patient,
 the first compartment comprising an entry capable of being assembled to an end of the first elongate flexible part,
 the second compartment comprising an exit associated with the entry of the first compartment, the second elongate flexible part being movable through the exit and the entry so as to extend into the first hollow tubular elongate flexible part, and
 the outer peripheral wall having an aperture which opens into the interior of the first compartment, through which the first elongate flexible part can be moved.

2. The medical robot according to claim 1, wherein the degree of freedom is a rotation about a vertical axis.

3. The medical robot according to claim 1, comprising a drive module adapted to generate movement of the second elongate flexible part relative to the container by at least a degree of freedom.

4. The medical robot according to claim 3, wherein the exit is associated with the entry via the drive module.

5. The medical robot according to claim 3, wherein a hollow introducer tube comprises a first end integral in translation with the inner peripheral wall and which can be assembled to said first end of the first elongate flexible part, and a second end assembled to an exit of the drive module.

6. The medical robot according to claim 3, wherein the second compartment comprises an outer peripheral wall, and wherein an intermediate space is defined between the outer peripheral wall of the second compartment and the inner peripheral wall, the drive module being housed within the intermediate space.

7. The medical robot according to claim 3, wherein each drive module can be operated to generate one and/or the other among a translational movement of the respective elongate flexible part along its axis and a rotational movement of the respective elongate flexible part about its axis.

8. The medical robot according to claim 7, wherein each drive module comprises a base defining an axis, and a mobile unit that is rotatable relative to the base with respect to this axis, the mobile unit comprising a movement application system that can be operated to generate translational movement of the respective elongate flexible part along this axis.

9. The medical robot according to claim 1, wherein the drive module is a second drive module, the medical robot further comprising a first drive module adapted to generate movement of the first elongate flexible part relative to the fixed base by at least a degree of freedom.

10. The medical robot according to claim 9, wherein the first drive module is assembled to the aperture.

11. The medical robot according to claim 9, comprising a motor adapted to drive the container for the degree of freedom, the second drive module and the motor being enslaved to one another.

12. The medical robot according to claim 9, wherein the hollow introducer tube is a second hollow introducer tube, and wherein a first hollow introducer tube comprises a first end secured to the outer peripheral wall and assembled to the aperture, and a second end assembled to the first drive module.

13. The medical robot according to claim 1, wherein the fixed base and the container are in the form of consumable and/or sterilizable elements.

14. The medical robot according to claim 1, wherein, in a second configuration, the second compartment comprises an exit separated from the entry of the first compartment, the second elongate flexible part being movable through the exit to extend within the first hollow tubular elongate flexible part.

15. The medical robot according to claim 14 wherein, in the second configuration, a ramp guides the second elongate flexible part parallel to the first elongate flexible part and externally thereto.

* * * * *